United States Patent [19]

Hirota et al.

[11] Patent Number: 4,786,494
[45] Date of Patent: Nov. 22, 1988

[54] SHAMPOO COMPOSITION

[75] Inventors: Hajime Hirota, Tokyo; Susumu Takaya, Funabashi, both of Japan

[73] Assignee: Kao Corporation, Tokyo, Japan

[21] Appl. No.: 815,982

[22] Filed: Jan. 3, 1986

[30] Foreign Application Priority Data

Jan. 25, 1985 [JP] Japan ................................ 60-12248

[51] Int. Cl.⁴ ...................... A61K 7/06; C08B 37/08; C08B 59/44
[52] U.S. Cl. ............................... 424/70; 424/DIG. 4; 424/59; 514/852; 514/864; 536/20; 536/91; 536/119
[58] Field of Search ................... 424/70; 536/119, 20, 536/91

[56]  References Cited
FOREIGN PATENT DOCUMENTS

| 0115888 | 8/1984 | European Pat. Off. | 424/70 |
| 53-6349 | 1/1978 | Japan | 424/70 |
| 54-134711 | 10/1979 | Japan | 424/70 |
| 59-184299 | 10/1984 | Japan | 424/70 |
| 2140452 | 11/1984 | United Kingdom | 424/70 |

OTHER PUBLICATIONS

Chemical Abstracts, vol. 102, No. 14, Apr. 1985, p. 383, Abstract No. 119422d.

Primary Examiner—Dale R. Ore
Attorney, Agent, or Firm—Flynn, Thiel, Boutell & Tanis

[57] ABSTRACT

A shampoo composition comprises a fatty acid ester of sucrose and a nonionic cellulose ether compound in addition to a shampoo base. It provides creamy foam and results in smooth combing and prevention of hair flying.

9 Claims, No Drawings

SHAMPOO COMPOSITION

The present invention relates to a shampoo composition. More particularly, the invention relates to a shampoo composition comprising an anionic surfactant or the like used as the base in which a sucrose/fatty acid ester surfactant and a nonionic cellulose ether derivative are incorporated so as to form smooth, creamy foams during shampooing, make smooth combing possible after shampooing and prevent shampooed, dried hair from flying.

STATEMENT OF PRIOR ARTS

Ordinary shampoo compositions contain as a base an anionic surfactant such as a salt of an alkyl sulfate or polyoxyethylenealkyl sulfate, a nonionic surfactant such as a polyoxyethylene alkyl ether or fatty acid alkylolamide, or an amphoteric surfactant such as an alkylbetaine or alkylamine oxide, alone or in the form of a mixture of them. However, the shampoo compositions containing these bases tend to remove sebaceous matters and other oils excessively from hair which harms the feel of the shampooed hair and makes smooth combing or brushing impossible. Further, the hair cannot be set easily after drying. Particularly in winter, in which the humidity of the air is low, hair is statically electrified by brushing which causes a hair flying phenomenon and, as a result, the hair is kinked and combing and brushing are made more difficult. Because of such troubles, the hair is split or broken. To overcome these defects, an oil or the like is incorporated in the shampoo base. However, the amount of oil or the like is limited and, as a matter of course, they are contained in a form emulsified or solubilized with a surfactant in the shampoo and, therefore, it is difficult to leave a sufficient amount of the oil on the scalp and hair.

In addition, when the oil is used in a large amount, the essential functions of the shampoo, i.e. foaming and deterging powers, are extremely reduced which damages the commercial value of the shampoo seriously, though the amount of the oil adsorbed on the hair is increased. Though various shampoo compositions containing a cationic polymer, etc. so as to exhibit a rinsing effect on the shampooed hair have been proposed recently, the shampooed hair has often a greasy touch under wet conditions and also has a sticky touch and causes flaking under dry conditions.

SUMMARY OF THE INVENTION

After intensive investigations made for the purpose of developing a shampoo composition which does not cause the kinking of hair during shampooing, thus facilitating shampooing, and which has conditioning effects which make smooth combing of the shampooed hair possible and smoothness hair by overcoming the defects of the conventional shampoo compositions, the inventors have found that, when a sucrose/fatty acid ester surfactant and a nonionic cellulose ether derivative are incorporated in an ordinary shampoo base selected from the group consisting of anionic surfactants, nonionic surfactants (excluding sucrose/fatty acid ester surfactant), cationic surfactants and amphoteric surfactants, smooth and creamy foams can be formed during shampooing, entanglement can be prevented which facilitates shampooing and conditioning effects can be obtained which smoothen the shampooed hair without causing a sticky feel after drying. The present invention has been completed on the basis of this finding.

The present invention provides a shampoo composition characterized by comprising:

(A) 0.1 to 10 wt. % of a sucrose/fatty acid ester surfactant of the general formula (1):

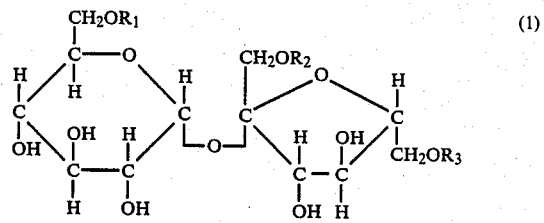

wherein at least one of $R_1$, $R_2$ and $R_3$ represents a straight-chain or branched, saturated or unsaturated acyl group having 8 to 24 carbon atoms and the balance represents a hydrogen atom, the $R_1$, $R_2$ and $R_3$ being either the same or different, and (B) 0.05 to 5 wt. % of one or a mixture of two or more nonionic cellulose ether derivatives of the general formula (2):

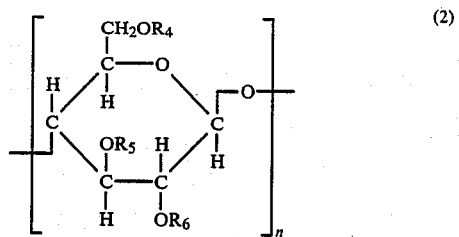

wherein $R_4$, $R_5$ and $R_6$ each represent a hydrogen atom, a group of the formula: $-(CH_2CH_2O)_mH$ in which m represents a number of 1 to 5, or a group of the formula: $-CH_3$ or $-C_3H_6OH$ and n is a number of 100 to 10,000, preferably 100 to 1,000.

A shampoo composition according to the invention comprises from 5 to 30 percent by weight of a shampoo base component, (A) 0.1 to 10 percent by weight of a fatty acid ester of sucrose, (B) 0.05 to 5 percent by weight of a nonionic cellulose ether compound and the balance water.

A conventional surfactant is used as the shampoo base component. Some examples thereof are listed below.

(1) salts of straight-chain or branched alkylbenzenesulfonic acids in which the alkyl group has 10 to 16 carbon atoms on the average, (2) salts of alkyl or alkenyl ether sulfates in which the straight-chain or branched alkyl or alkenyl group has 10 to 20 carbon atoms on the average and to which is added 0.5 to 8 mol, on the average per molecule, of ethylene oxide, propylene oxide, butylene oxide, a combination of ethylene oxide with propylene oxide in a ratio of 0.1/9.9 to 9.9/0.1 or a combination of ethylene oxide with butylene oxide in a ratio of 0.1/9.9 to 9.9/0.1, (3) salts of alkyl or alkenyl sulfates in which the alkyl or alkenyl group has 10 to 20 carbon atoms on the average, (4) salts of olefinsulfonic acids having 10 to 20 carbon atoms on the average in the molecule, (5) salts of alkanesulfonic acids having 10 to 20 carbon atoms on the average in the molecule, (6) salts of saturated or unsaturated fatty acids having 10 to 24 carbon atoms on the average in the molecule, (7) salts of alkyl or alkenyl ether carboxylates in which the alkyl or alkenyl group has 10 to 20 carbon atoms on the average and to which is added 0.5 to 8 mol, on the average per molecule, of ethylene oxide, propylene oxide, butylene oxide, a combination of ethylene oxide with propylene oxide in a ratio of 0.1/9.9 to 9.9/0.1 or a combination of ethylene oxide with butylene oxide in a ratio of 0.1/9.9 to 9.9/0.1, (8) salts and esters of α-sulfo fatty acids of the following formula:

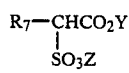

in which Y represents an alkyl group having 1 to 3 carbon atoms or a counter ion and $R_7$ represents an alkyl or alkenyl group having 1 to 20 carbon atoms, Wherein the counter ions of the anionic surfactants include, for example, alkali metal ions such as sodium and potassium, alkaline earth metal ions such as calcium and magnesium, ammonium ion and alkanolamines having 1 to 3 alkanol groups and 2 or 3 carbon atoms, such as monoethanolamine, diethanolamine, triethanolamine and triisopropanolamine, (9) amino acid-type surfactants of the following general formula:

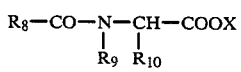         (i)

in which $R_8$ represents an alkyl or alkenyl group having 8 to 24 carbon atoms, $R_9$ represents a hydrogen atom or an alkyl group having 1 or 2 carbon atoms, $R_{10}$ represents an amino acid residue and X represents an alkali metal or alkaline earth metal ion,

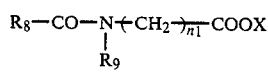         (ii)

in which $R_8$, $R_9$ and X are as defined above and $n_1$ represents an integer of 1 to 5,

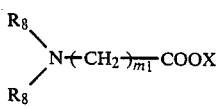         (iii)

in which $R_8$ and X are as defined above and $m_1$ represents an integer of 1 to 8,

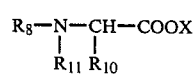         (iv)

in which $R_8$, $R_{10}$ and X are as defined above and $R_{11}$ represents a hydrogen atom or an alkyl or hydroxyalkyl group having 1 or 2 carbon atoms,

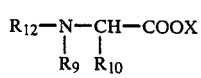         (v)

in which $R_9$, $R_{10}$ and X are as defined above and $R_{12}$ represents a β-hydroxyalkyl or β-hydroxyalkenyl group having 6 to 28 carbon atoms,

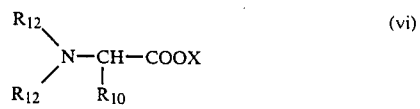         (vi)

in which $R_{10}$, $R_{12}$ and X are as defined above, (10) phosphoric ester surfactants:

(i) acid alkyl (or alkenyl) phosphates of the formula:

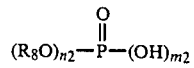

in which $R_8$ is as defined above and $n_2$ and $m_2$ each represent such a number that the total of them is 3 and $n_2$ represents a number of 1 or 2, (ii) Alkyl (or alkenyl) phosphates of the formula:

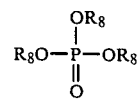

in which $R_8$ is as defined above, (iii) salts of alkyl (or alkenyl) phosphates of the formula:

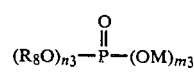

in which $R_8$ is as defined above, M represents sodium, potassium or calcium, $n_3$ and $m_3$ each represent such a number that the total of them is 3 and $n_3$ represents a number of 1 to 3,

(11) sulfonic acid-type amphoteric surfactants of the formula:

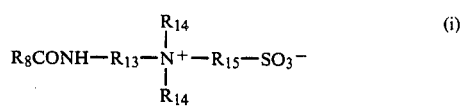         (i)

in which $R_8$ is as defined above, $R_{13}$ represents an alkylene group having 1 to 4 carbon atoms, $R_{14}$ represents an alkyl group having 1 to 5 carbon atoms and $R_{15}$ represents an alkylene or hydroxyalkylene group having 1 to 4 carbon atoms,

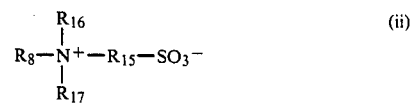         (ii)

in which $R_8$ and $R_{15}$ are as defined above and $R_{16}$ and $R_{17}$ represent each an alkyl or alkenyl group having 8 to 24 or 1 to 5 carbon atoms,

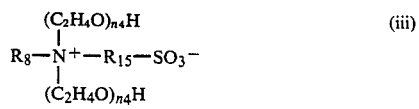         (iii)

in which $R_8$ and $R_{15}$ are as defined above and $n_4$ represents an integer of 1 to 20,

(12) betaine-type amphoteric surfactants of the following general formula:

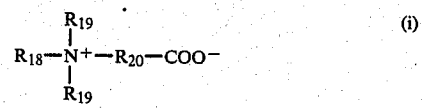

in which $R_{18}$ represents an alkyl, alkenyl, β-hydroxyalkyl or β-hydroxyalkenyl group having 8 to 24 carbon atoms, $R_{19}$ represents an alkyl group having 1 to 4 carbon atoms and $R_{20}$ represents an alkylene or hydroxyalkylene group having 1 to 6 carbon atoms,

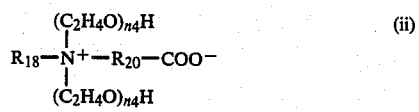

in which $R_{18}$, $R_{20}$ and $n_4$ are as defined above,

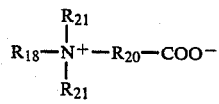

in which $R_{18}$ and $R_{20}$ are as defined above and $R_{21}$ represents a carboxyalkyl or hydroxyalkyl group,

(13) polyoxyethylene alkyl or alkenyl ethers in which the alkyl or alkenyl group has 10 to 20 carbon atoms on the average and to which 1 to 20 mol of ethylene oxide is added,

(14) polyoxyethylene alkylphenyl ethers in which the alkyl group has 6 to 12 carbon atoms on the average and to which 1 to 20 mol of ethylene oxide is added,

(15) polyoxypropylene alkyl or alkenyl ethers in which the alkyl or alkenyl group has 10 to 20 carbon atoms on the average and to which 1 to 20 mol of propylene oxide is added,

(16) polyoxybutylene alkyl or alkenyl ethers in which the alkyl or alkenyl group has 10 to 20 carbon atoms on the average and to which 1 to 20 mol of butylene oxide is added,

(17) nonionic surfactants having an alkyl or alkenyl group having 10 to 20 carbon atoms on the average and to which 1 to 30 mol, in total, of a combination of ethylene oxide with propylene oxide or a combination of ethylene oxide with butylene oxide is added (the ratio of ethylene oxide to propylene or butylene oxide being 0.1/9.9 to 9.9/0.1),

(18) higher fatty acid alkanolamides of the following formula and alkylene oxide adducts thereof:

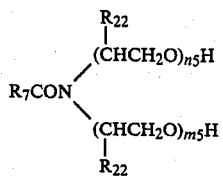

in which $R_7$ is as defined above, $R_{22}$ represents a hydrogen atom or a methyl group, $n_5$ represents an integer of 1 to 3 and $m_5$ represents an integer of 0 to 3,

(19) fatty acid/glycerol monoesters comprising a fatty acid having 10 to 20 carbon atoms on the average and glycerol,

(20) alkylamine oxides of the following formula:

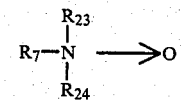

in which $R_7$ is as defined above and $R_{23}$ and $R_{24}$ represent each an alkyl group having 1 to 3 carbon atoms,

(21) cationic surfactants of the following formula:

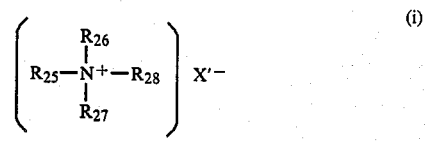

in which at least one of $R_{25}$, $R_{26}$, $R_{27}$ and $R_{28}$ represent an alkyl or alkenyl group having 8 to 24 carbon atoms and the balance represents an alkyl group having 1 to 5 carbon atoms and X' represents a halogen atom,

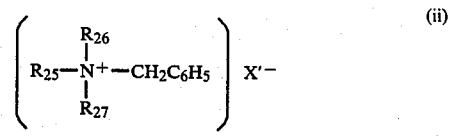

in which $R_{25}$, $R_{26}$, $R_{27}$ and X' are as defined above,

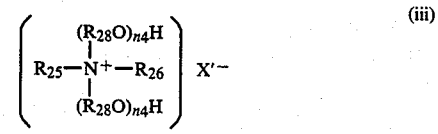

in which $R_{25}$, $R_{26}$, X' and $n_4$ are as defined above and $R_{28}$ represents an alkylene group having 2 to 3 carbon atoms.

Among the above-mentioned shampoo bases, particularly preferred are anionic surfactants such as salts of straight-chain or branched alkyl surfactants having 10 to 16 carbon atoms on the average, salts of polyoxyethylene alkyl sulfates in which the alkyl group has 8 to 20 carbon atoms on the average (average molar number of addition: 0.5 to 8), alkyl phosphates having 8 to 16 carbon atoms on the average and salts of olefinsulfonic acids having 10 to 16 carbon atoms on the average; nonionic surfactants such as higher fatty acid mono- or dialkanolamides in which the alkyl group has 10 to 14 carbon atoms; and amphoteric surfactants of alkylamine oxide, alkylbetaine and imidazoline types: The above-mentioned shampoo bases may be used either alone or in the form of a mixture of two or more of them and their concentration is 5 to 30% (by weight; the same shall apply hereinafter), preferably 10 to 25%, based on the shampoo composition.

The sucrose/fatty acid ester surfactants of the above general formula (I) used in the present invention comprises usually a mixture of a mono-, di- and tri-acylated compounds. The acyl groups $R_1$, $R_2$ and $R_3$ have preferably 12 to 18 carbon atoms and the ratio of the monoacylated compound to the di- or triacylated compound is preferably 70/30 to 30/70.

The amount of the sucrose/fatty acid ester used in the present invention is 0.1 to 10%, preferably 0.2 to 5%, based on the shampoo composition.

Examples of the preferred nonionic cellulose ether derivatives of the above general formula (2) used as the component (B) in the present invention include hydroxyethylcellulose, hydroxypropylcellulose, hydroxypropylmethylcellulose and methylcellulose.

Among the above-mentioned cellulose derivatives, hydroxyethylcellulose is available on the market under the name of "Cellosize" (Union Carbide Corp.) or "Natrosol" (Hercules). To attain the object of the present invention, those in which 1.0 to 4.0, particularly 1.8 to 3.0, molecules of ethylene oxide is added per glucose residue are preferred.

It is preferable that the methylcellulose have a content, based on the total weight of $-OR4$, $-OR5$ and $-OR6$ in the formula (2), of methoxy group (methylation extent) in the range of 10 to 40 wt.%, particularly 20 to 30 wt.%. Hydroxypropylcellulose is preferred to have a content of hydroxpropoxy group of 1 to 20 wt.%, particularly 5 to 15 wt.%.

The nonionic cellulose ether compound (B) may have any of $-R4$, $-R5$ and $-R6$ at either terminals of the molecule having the formula (2). The component (B) may be used, mixed with another nonionic cellulose ether compound of the formula (2). The component (B) is used in an amount of 0.05 to 5 wt.%, preferably 0.1 to 2 wt.%.

The form of the composition of the present invention must be a paste or a liquid containing water as the medium. The amount of water is preferably 40 to 90% and the pH of the liquid is preferably 4 to 8.

The shampoo composition of the present invention may contain, in addition to the above-mentioned indispensable components, other known constituents of shampoos such as solubilizers, e.g., propylene glycol, glycerol or urea, viscosity modifiers, e.g., ethanol, inorganic salts, higher alcohols or polyacrylic acids, perfumes, colorants, U.V. absorbers, antioxidants, dandruff removers, sterilizers and antiseptics.

EXAMPLES

The following examples will further illustrate the present invention, which by no means limit the invention.

In the following examples, the properties of the shampoos were evaluated as follows:

(1) Feel of foams:

30 g of human hair was wet with water (40° C.) to impregnate it with 20 g of water. Then, the hair was shampooed with 1 g of a shampoo composition and the feel of the foams was judged by 20 female panelists organoleptically.

Items:

The easiness of passing the fingers through hair during shampooing was shown in terms of "slippiness of foams" and the appearance of the foams was evaluated from the viewpoint of "creaminess".

Criteria of the evaluation:

O The smoothness of the foams was superior to that of the standard or the appearance of the foams was creamy.

X The smoothness and appearance of the foams were equivalent to that of the standard.

Standard:

| | |
|---|---|
| sodium polyoxyethylene (3) lauryl sulfate | 15% |
| coconut fatty acid diethanolamine | 3 |
| flavor | a suitable amount |
| water | the balance (pH 7.2) |

(2) Easiness of combing:

30 g of human hair was shampooed by shaking in 10 cc of an aqueous solution of a shampoo composition (concentration: 10%) for about 30 sec, then rinsed in running water for 1 min, squeezed and arranged on a stain gauge. The hair was combed and the force required for the combing was measured (wet test). Separately, the hair rinsed in running water was squeezed, dried with a dryer and left to stand in an air-conditioned room at 25° C. overnight while the relative humidity was kept at 65% and the hair was arranged on the strain gauge. The hair was combed and the force required for the combing was measured (dry test).

The lower the load, the easier the combing.

(3) Hair flying:

A change of the hair by the static electricity in the dry test of the easiness of combing was observed macroscopically.

O: No hair flying was caused at all.

X: Hair flying was recognized.

EXAMPLE 1

Shampoo compositions as shown in Table 1 were prepared by an ordinary process and the effects of the indispensable components were examined to obtain the results shown in Table 1.

TABLE 1

| No. | Examples of the present invention | | | Comparative Examples | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Components (%) | | | | | | | | | | | | |
| triethanolamine polyoxyethylene(3)lauryl sulfate | 15 | | | 15 | 15 | 15 | | | | 15 | 15 | 15 |
| triethanolamine α-olefin (C16) sulfonate | | 15 | | | | | | 15 | | | | |
| Ammonium polyoxyethylene (3)lauryl ether carboxylate | | | 15 | | | | 15 | | | | | |
| ester of sucrose and fatty acid (lauric acid as fatty acid) (ratio of mono to di and tri = 7/3) | 0.5 | 0.5 | 0.5 | — | 0.5 | 15 | 0.5 | 0.05 | 0.5 | 1.0 | — | — |
| Methylcellulose (viscosity of 2% aqueous solution: 4,000 cP) | 0.5 | 0.5 | 0.5 | 0.5 | — | 0.5 | 6 | 0.5 | 0.03 | — | 1.0 | — |

TABLE 1-continued

| | Examples of the present invention | | | Comparative Examples | | | | | | | | |
|---|---|---|---|---|---|---|---|---|---|---|---|---|
| No. | 1 | 2 | 3 | 4 | 5 | 6 | 7 | 8 | 9 | 10 | 11 | 12 |
| Perfume, water | | | | | | | the balance | | | | | |
| Properties | | | | | | | | | | | | |
| Touch of foams | | | | | | | | | | | | |
| Slippiness | | | | X | X | X | X | X | X | X | X | X |
| Creaminess | | | | X | X | X | X tacky | X | X | X | X | X |
| Finish | | | | | | | | | | | | |
| Combing easiness (wet) (g) | 178 | 180 | 174 | 472 | 406 | 190 | 342 | 396 | 412 | 388 | 442 | 480 |
| Combing easiness (dry) (g) | 82 | 84 | 88 | 286 | 200 | 92 | 128 | 248 | 222 | 244 | 280 | 296 |
| Hair flying | | | | X | X | | X | X | X | X | X | X |

EXAMPLE 2

A shampoo composition as shown below was prepared and the effects of various sucrose/fatty acid ester surfactants were examined to obtain the results shown in Table 2.

Composition:

| | |
|---|---|
| triethanolamine lauryl sulfate | 15% |
| lauric acid diethanolamide | 5 |
| hydroxyethylcellulose (viscosity of 1% aqueous solution: 2,400 cP) | 0.8 |
| sucrose/fatty acid ester (see Table 2) | 1 |
| fragrance | a suitable amount |
| water | to balance (pH 7.5) |

EXAMPLE 3

A shampoo composition as shown below was prepared and the effects of various nonionic cellulose ether derivatives were examined to obtain the results shown in Table 3.

Composition:

| | |
|---|---|
| triethanolamine α-olefin (C16) sulfonate | 15% |
| nonionic cellulose ether derivative (see Table 3) | 0.5 |
| ester of sucrose and fatty acid (palmitic acid as fatty acid) (ratio of mono to di and tri = 50/50) | 0.7 |
| fragrance | a suitable amount |
| water | the balance (pH 5.0) |

TABLE 2

| | Sucrose/fatty acid ester | | Properties | | | | |
|---|---|---|---|---|---|---|---|
| | | ratio of mono to | Touch of foams | | Easiness of combing | | Hair |
| | Fatty acid | di and tri | Slippiness | Creaminess | Wet | Dry | flying |
| Examples of the present invention | Lauric acid | 100/0 | | | 210 | 98 | |
| | " | 60/40 | | | 180 | 78 | |
| | " | 30/70 | | | 198 | 94 | |
| | " | 0/100 | | | 214 | 100 | |
| | Palmitic acid | 70/30 | | | 198 | 92 | |
| | " | 30/70 | | | 208 | 98 | |
| | Stearic acid | 60/40 | | | 188 | 82 | |
| | Eicosanoic acid | 70/30 | | | 228 | 104 | |
| | Behenic acid | 50/50 | | | 232 | 112 | |
| Comparative Example | No ester added | | X | X | 468 | 284 | X |

TABLE 3

| | | Properties | | | | |
|---|---|---|---|---|---|---|
| | nonionic cellulose ether derivative | Touch of foams | | Easiness of combing | | Hair flying |
| | | Slippiness | Creaminess | Wet | Dry | |
| Examples of the present invention | Hydroxyethylcellulose (viscosity of 1% aqueous solution: 5,000 cP) | | | 192 | 88 | |
| | Hydroxyethylcellulose (viscosity of 1% aqueous solution: 10,000 cP) | | | 178 | 82 | |
| | Hydroxypropylmethylcellulose (viscosity of 1% aqueous solution: 6,000 cP) | | | 182 | 78 | |
| | Hydroxypropylmethylcellulose (viscosity of 1% aqueous solution: 12,000 cP) | | | 188 | 92 | |
| | Methylcellulose (viscosity of 2% aqueous solution: 4,000 cP) | | | 180 | 86 | |
| | Hydroxypropylcellulose (viscosity of 2% aqueous | | | 178 | 84 | |

TABLE 3-continued

| | nonionic cellulose ether derivative | Properties | | | | |
|---|---|---|---|---|---|---|
| | | Touch of foams | | Easiness of combing | | Hair flying |
| | | Slippiness | Creaminess | Wet | Dry | |
| Comparative Example | solution: 2,500 cP) Not used | X | X | 398 | 236 | X |

The embodiments of the invention in which an exclusive privilege or property is claimed are defined as follows:

1. A shampoo composition comprising
    (A) 0.1 to 10 percent by weight of a mixture of mono-, di- and tri-acylated fatty acid esters of sucrose having the formula (1)

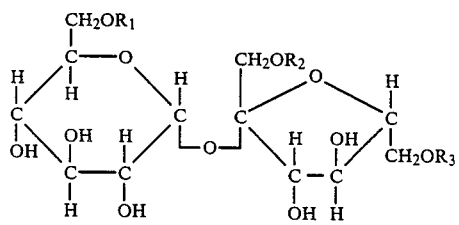

in which $R_1$, $R_2$ and $R_3$ represent hydrogen or a straight-chain or branched, saturated or unsaturated acyl group having 8 to 24 carbon atoms and the weight ratio of mono-acylated esters to the sum of di- and tri-acylated esters is 70/30 to 30/70,
    (B) 0.05 to 5 percent by weight of a nonionic cellulose ether compound having the formula (2)

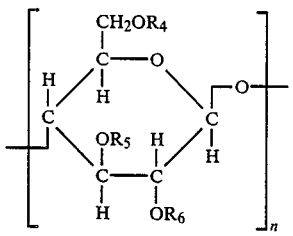

in which $R_4$, $R_5$ and $R_6$ is a hydrogen atom, $(CH_2CH_2O)_mH$ in which m is 1 to 5, $-CH_3$ or $-C_3H_6OH$, and n is 100 to 10,000,
    (C) 5 to 30 percent by weight of a shampoo base comprising one or more members selected from the group consisting of anionic surfactants, cationic surfactants, nonionic surfactants and amphoteric surfactants, and
    (D) water.

2. The shampoo composition of claim 1, in which the nonionic ether compound is a cellulose derivative selected from the group consisting of hydroxyethylcellulose derivatives, hydroxypropylcellulose derivatives, hydroxypropylmethylcellulose derivatives and methylcellulose derivatives.

3. The shampoo composition of claim 1, in which said acyl group is straight-chained and has 12 carbon atoms, said nonionic cellulose ether compound is a derivative of methylcellulose and said shampoo base is ammonium polyoxyethylene lauryl ether carboxylate.

4. The shampoo composition of claim 1, in which said acyl group is straight-chained and has 12 carbon atoms, said nonionic cellulose ether compound is a derivative of methylcellulose and said shampoo base is triethanolamine polyoxyethylene lauryl sulfate.

5. The shampoo composition of claim 4, in which the cellulose derivative has from 1.8 to 3.0 molecules of ethylene oxide added per glucose residue.

6. A shampoo composition as claimed in claim 1, in which a content of methoxy group, based on the total of $-OR_4$, $-OR_5$ and $-OR_6$, in (B) the nonionic cellulose ether compound is 10 to 40 percent by weight.

7. A shampoo composition as claimed in claim 1, which has a pH of 4 to 8.

8. A shampoo composition as claimed in claim 1, which comprises 40 to 90 percent by weight of water.

9. A shampoo composition as claimed in claim 1, in which n is from 100 to 1,000 in the formula (2).

* * * * *